United States Patent [19]
Löffler et al.

[11] Patent Number: 5,965,422
[45] Date of Patent: Oct. 12, 1999

[54] LYSOPHOSPHOLIPASE PRODUCED FROM ASPERGILLUS BY RECOMBINANT METHODS

[75] Inventors: Fridolin Löffler, Bensheim; Quoc Khanh Nguyen, Reichelsheim; Erwin Schuster, Bensheim-Auerbach; Bruno Sprössler, Roßdorf, all of Germany; Lutz Thomas, North Brunswick, N.J.; Sabine Wolf, Otzberg, Germany

[73] Assignee: Rohm GmbH, Darmstadt, Germany

[21] Appl. No.: 08/859,106

[22] Filed: May 20, 1997

[30] Foreign Application Priority Data

May 22, 1996 [DE] Germany .................. 196 20 649

[51] Int. Cl.⁶ .................. C12N 15/09; C12N 15/55; C12N 15/63
[52] U.S. Cl. .................. 435/198; 435/320.1; 435/243; 435/254.11; 435/254.3; 536/23.2
[58] Field of Search .................. 536/23.2; 435/320.1, 435/243, 195, 196, 197, 198, 254.11, 254.3, 320.2

[56] References Cited

FOREIGN PATENT DOCUMENTS 0 219 269   4/1987   European Pat. Off. .

OTHER PUBLICATIONS

G. Konieczny–Janda and G. Richter, "Progress in the Enzymatic Saccharification of Wheat Starch," *Starke* 43, No. 8, pp. 308–315 (1991).

*Primary Examiner*—Keith D. Hendricks
*Assistant Examiner*—Bradley S. Mayhew
*Attorney, Agent, or Firm*—Burns, Doane, Swecker & Mathis, L.L.P.

[57] ABSTRACT

This invention relates to a recombinant deoxyribonucleic acid (DNA) isolatable from Aspergillus, preferably *Aspergillus foetidus*, wherein it codes for a lysophospholipase (LPL) and has the nucleotide sequence for mature LPL stated in SEQ ID NO:1 or a nucleotide sequence derived therefrom, which hybridises under stringent conditions with the nucleotide sequence for mature LPL stated in SEQ ID NO:1. The invention also relates to vectors, to transformed host organisms and to processes for the production of LPL. The invention also provides enzyme products for the production of maltose syrup and products produced in this manner.

14 Claims, 3 Drawing Sheets

LYSOPHOSPHOLIPASE PRODUCED FROM ASPERGILLUS BY RECOMBINANT METHODS

DESCRIPTION

This invention relates to a recombinant deoxyribonucleic acid (DNA) prepared from Aspergillus, preferably from *Aspergillus foetidus*, which codes for a lysophospholipase (LPL, phospholipase B, 2-lysophosphatidylcholine acylhydrolase, IUB 3.1.1.5), to vectors which contain this DNA together with further DNA sequences to express the LPL gene, and to filamentous fungi transformed with these vectors and capable of expressing the recombinant DNA. The invention furthermore relates to enzyme products which contain recombinant LPL produced by means of the recombinant filamentous fungi and to a process to improve the filtration of starch hydrolysates by means of the recombinant LPL.

During the production of starch hydrolysates, the problem arises of filtering out any turbidity remaining in the resultant highly concentrated solution of glucose oligomers. This turbidity consists partially or entirely of phospholipids, which are hydrolysed by phospholipid-cleaving enzymes, so accelerating the filtration operation.

Phospholipid-cleaving enzymes suitable for this application are described in EP 0 219 269 and by Konieczny-Janda, G. and Richter, G.: *Starch/Stärke* (1991), 43(8), pp. 308–315. EP 0 219 269 describes a phospholipase from *Aspergillus niger*, which contains xylanase and β-glucanase in appropriate ratios and raises the filtration yield when clarifying maltose syrup from 100 to 300 l/hm$^2$. Konieczny-Janda and Richter isolated an enzyme from *Aspergillus niger* glucoamylase which partially hydrolyses the lysophospholipids of wheat starch, such that the insoluble constituents aggregate so rendering them filterable. The isolated enzyme cleaves wheat lipids and synthetic lysophospholipids.

The object underlying this invention is to provide a low cost lysophospholipase for the filtration of starch syrup, especially maltose syrup obtained by treating maltodextrin solutions with β-amylase. The lysophospholipase should furthermore contain neither glucoamylases nor transglucosidases. It should moreover be possible to produce the lysophospholipase in large quantities by means of a transformed host organism. It should be possible to use the enzyme to produce preparations which are particularly suitable for hydrolysing lysophospholipids and thus for clarifying starch hydrolysates.

This object is achieved according to the invention by a recombinant deoxyribonucleic acid (DNA) isolatable from Aspergillus which is characterised in that it codes for a lysophospholipase (LPL) and has the nucleotide sequence for mature LPL stated in SEQ ID NO:1 or a nucleotide sequence derived therefrom, which hybridises under stringent conditions with the nucleotide sequence for mature LPL stated in SEQ ID NO:1. The DNA is preferably isolated from *Aspergillus foetidus*.

Using this DNA, it is possible to produce vectors, in particular plasmids, with which Aspergillus strains or *Trichoderma reesei* strains may be transformed. Those strains expressing and secreting large quantities of LPL may then be selected from among the resultant transformants. These transformed host organisms in turn allow LPL to be produced in large quantities. Enzyme products containing LPL which are particularly suitable for hydrolysing lysophospholipids may be produced from the resultant fermentation liquors. By selection of the host organism, it is possible to produce the lysophospholipase at high yield and substantially without any content of disruptive enzymes such as glucoamylases and transglucosidases, such that it is possible using the enzyme product produced according to the invention to accelerate the filtration of maltose syrup to a greater extent and simultaneously to produce fewer unwanted secondary products in the clarified syrup than is possible with conventionally produced preparations.

BRIEF DESCRIPTION OF THE DRAWINGS

The following figures illustrate the invention in greater detail.

DEPOSITED MICROORGANISMS

The following microorganisms were deposited in accordance with the provisions of the Budapest Treaty with Deutscher Sammlung von Mikroorganismen und Zellkulturen (DSM), Mascheroder Weg 1B, 38124 Braunschweig, Germany:

A. foetidus RH 3046: deposition no. DSM 10652

E. coil DH5α pKC3: deposition no. DSM 10653

E. coli DH5α pKC9: deposition no. DSM 10654

E. coli DH5α pKC12: deposition no. DSM 10655.

Recombinant DNA

This invention relates to a recombinant deoxyribonucleic acid (DNA) isolatable from *Aspergillus foetidus* which is characterised in that it codes for a lysophospholipase (LPL) and has the nucleotide sequence for mature LPL stated in SEQ ID NO:1 or a nucleotide sequence derived therefrom, which hybridises under stringent conditions with the nucleotide sequence for mature LPL stated in SEQ ID NO:1.

The sequence shown in SEQ ID NO:1 corresponds to the chromosomal LPL gene from *A. foetidus* RH 3046 with 5'- and 3'-flanking sequences. The nucleotide sequence for the mature LPL is taken to be the DNA sequence obtained according to SEQ ID NO:1 which codes for the structural gene of LPL without the signal peptide. The nucleotide sequence for the mature LPL thus comprises those exon sequences which code for amino acids 1 (Ser) to 270 (Leu).

This invention moreover relates to a nucleotide sequence derived from the nucleotide sequence for mature LPL. This should be taken to be nucleotide sequences which differ from the nucleotide sequence stated in SEQ ID NO:1, but which hybridise under stringent conditions with this DNA for LPL.

The phrase "stringent hybridisation conditions" is familiar to the person skilled in the art (c.f. for example Maniatis et al., (1982), *Molecular Cloning, A Laboratory Manual*, Cold Spring Harbor Laboratory, New York). Stringent hybridisation conditions are those conditions under which only those DNA molecules which are highly homologous, for example >85%, hybridise with each other. The stringency of the test conditions may be established, for example, by the hybridisation temperature or by the salt concentration of the hybridisation solution.

DNA sequences derived from the LPl structural gene may, for example, exhibit deviations in the nucleotide sequence determined by the degeneration of the genetic code without exhibiting deviations in the amino acid sequence. Slight deviations in the nucleotide sequence may also result in structurally irrelevant changes in the amino acid sequence of the enzyme. Largely homologous genes which may be isolated by means of the present invention from other strains of *A. foetidus* or closely related Aspergillus species are thus included. The invention also includes fusion proteins which contain parts of the LPL gene essential to the enzymatic function of the protein or nucleotide sequences derived therefrom. The sequence description according to SEQ ID NO:1 furthermore contains the signal peptide coding sequence upstream from the nucleotide sequence for mature LPL, beginning with amino acid 1 (Met) to 21 (Pro). There then follows a propeptide having six amino acids from position 22 (Ala) to 27 (Arg). The functional promoter region of the LPL gene (nucleotide 1 to 1608) lies upstream from the signal peptide sequence. Downstream from the structural gene, there is the TAA stop codon and a region functioning as a transcription terminator (nucleotides 2654 to 3650). The sequence description according to SEQ ID NO:1 reproduces the entire amino acid sequence for LPL with the signal peptide.

The recombinant DNA according to the invention may be obtained by isolating an LPL gene from the genome of an LPL-producing Aspergillus strain, in particular an *A. foetidus* strain, for example from *A. foetidus* RH 3046. To this end, RNA and/or DNA is obtained from the cell material of the Aspergillus strain.

In order to isolate the RNA, the cell material is preferably cultured in a medium in which the strain produces as much LPL as possible, as the content of LPL-specific RNA is higher in this induced cell material than in uninduced cell material. In this manner, a higher proportion of LPL-specific cDNA is obtained during cDNA synthesis, so facilitating isolation of the LPL cDNA.

Suitable culture media are, for example, minimal media for fungi, to which constituents containing lysolecithin, for example a soya fraction, have been added. Once the maximum LPL titre in the medium has been reached, the cells are advantageously harvested by freezing the filtered mycelium in liquid nitrogen.

RNA may be prepared from the cell material in a manner known per se. To this end, the mycelium is, for example, homogenised under liquid nitrogen in the presence of detergents such as SDS (sodium dodecylsulphate) and the RNA isolated by phenol, phenol/chloroform extractions, optionally with the addition of isoamyl alcohol. The RNA is then precipitated from the aqueous phase by adding salts, such as for example lithium chloride.

A complementary single-stranded DNA may first be produced from the RNA in a manner known per se by means of reverse transcriptase (RNA-dependent DNA polymerase). To this end, the RNA is incubated with a mixture of deoxynucleoside triphosphates (dATP, dCTP, dGTP and dTTP), an oligo(dT) primer, which hybridises with the poly(A) end of the mRNA, and a reverse transcriptase, for example the reverse transcriptase from the Moloney murine leukaemia virus (Mo-MuLV), which produces a complementary single-stranded DNA.

In a second stage, a complementary strand to the single-stranded DNA is in turn synthesised with DNA polymerase, so producing a double-stranded cDNA. The yield of LPL-specific cDNA may be multiplied by means of Taq-DNA polymerase in a manner known per se using the polymerase chain reaction (PCR). To this end, the single-stranded cDNA is incubated with a mixture of deoxynucleoside triphosphates, an appropriate partial sequence of the oligo (dT) primer for the reverse reaction and an LPL-specific primer for the forward reaction. The LPL-specific primer is derived from the amino acid sequence of the LPL and should theoretically hybridise only with a specific region of the single-stranded LPL-cDNA. cDNA synthesis is started with the Taq-DNA polymerase and thus proceeds only within a defined region, i.e. between two oligonucleotides. The PCR products are purified and inserted into plasmid pUC18. Once transformed into *E. coli* DH5α, the plasmid DNA may be prepared from the selected colonies and then hybridised with a radioactively labelled DNA probe. The cDNA insertion of a positive clone is sequenced. Correspondence of the amino acid sequence derived from the nucleotide sequence with the sequence determined by Edman degradation confirms the desired LPL gene.

The resultant LPL-cDNA may be used as a gene probe for Southern hybridisation and genomic cloning of the LPL.

The chromosomal LPL gene may be isolated by direct cloning of the chromosomal DNA hydrolysed with restriction enzymes in plasmid pUC18.

Genomic DNA may be obtained from the mycelium, irrespective of the cell culture conditions. It is preferred to culture the cell material in a complete medium for fungi, for example Sabouraud's medium. The DNA may be isolated from the cell material in a manner known per se by homogenisation of the cell material in a buffer, for example 100 mM tris-HCl, pH 7.5, 300 mM NaCl, 200 mM EDTA, and subsequent extraction with phenol, chloroform/isoamyl alcohol. The DNA is precipitated from the aqueous phase by adding ethanol and sodium acetate. It is completely cleaved with a restriction enzyme, for example BamHI and then fractionated by size in a sucrose gradient. On the basis of the results from Southern hybridisation, those fractions having DNA fragments of a size of approx. 9 to 10 kb are collected. Once the DNA has been precipitated with ethanol, the DNA is inserted into the vector pUC18. After transformation into *E. coli* DH5α, the desired LPL transformants may be identified by colony hybridisation. The isolated DNA is characterised in a manner known per se by restriction analysis and subsequent sequencing, for example using the Sanger method.

The position of the exon and intron sequences may be determined by comparing the cDNA sequence with the sequence of the chromosomal gene.

Vectors for expressing LPL in As illus or *T. reesei* strains

This invention also relates to a vector containing
a) DNA sequences to replicate the vector in *E. coli*,
b) DNA sequences to express and secrete a polypeptide in an Aspergillus strain or a *Trichoderma reesei* strain which code for a promoter, a signal peptide sequence and optionally for a terminator,
c) a polypeptide-coding DNA sequence which is functionally associated with the DNA sequences according to b), which vector is characterised in that the DNA sequence according to c) has a nucleotide sequence corresponding to the nucleotide sequence for mature LPIL stated in SEQ ID NO:1 or a nucleotide sequence derived therefrom, which hybridises under stringent conditions with the nucleotide sequence for mature LPL stated in SEQ ID NO:1.

The DNA sequences according to a) are required in order to be able to multiply the vector DNA in *E. coli*, for example *E. coli* DH5α. One such DNA sequence may be a phage, for example phage EMBL3, a cosmid or, preferably, a plasmid. Suitable plasmids are, for example, pBR322, pUC18 or pUC19 or optionally fragments of these plasmids, which contain at Least the replication origin and a selection marker for *E. coli*.

The vectors also contain DNA sequences according to b), which, in Aspergillus strains or *T. reesei* strains, give rise to the expression and secretion of the gene product of the LPL gene according to c). These DNA sequences according to b) are functionally associated with the LPL gene. They are, for example, 5'- and 3'-flanking sequences, such as promoters 5' of the gene, a signal peptide sequence, terminators 3' of the gene. Further functional DNA sequences which may be present are, for example, ribosome binding sites for translation, enhancers or "upstream activating sequences" or polyadenylation functions.

Signal peptide sequences are DNA sequences located at the 5' end immediately upstream from the structural gene which codes for amino acids, occur in extracellular proteins and are transcribed and translated together with the structural gene. When the protein is secreted from the cell, the signal peptide sequences are cleaved, so yielding the actual "mature" protein. A signal peptide sequence is thus necessary in order to ensure that the LPL is secreted from the host cell. A promoter and a terminator are also necessary to initiate translation and terminate transcription of the gene, respectively.

The promoter, the signal peptide sequence and/or the terminator may be those of the LPL gene naturally occurring in the chromosome of A. foetidus. The functional DNA sequences may also originate from other genes, the products of which are expressed and secreted in fungal strains of the genus Aspergillus or in T. reesei.

Examples of genes having suitable functional DNA sequences are, for example, the TAKA-amylase A gene from A. oryzae (EP 0 238 023), the pectinesterase gene or the polygalacturonidase gene from A. niger (EP 0 388 593), the glucoamylase gene from A. awarnori (EP 0 215 594), the cellobiohydrolase gene I (cbh 1) from T. reesei (EP 0 244 234).

The DNA sequence according to c) contains the LPL structural gene or a DNA sequence derived therefrom. This DNA sequence may, for example, be present in the form of a chromosomal gene with the naturally occurring introns or as cDNA without introns and derived from the messenger ribonucleic acid (mRNA).

Figure 1:
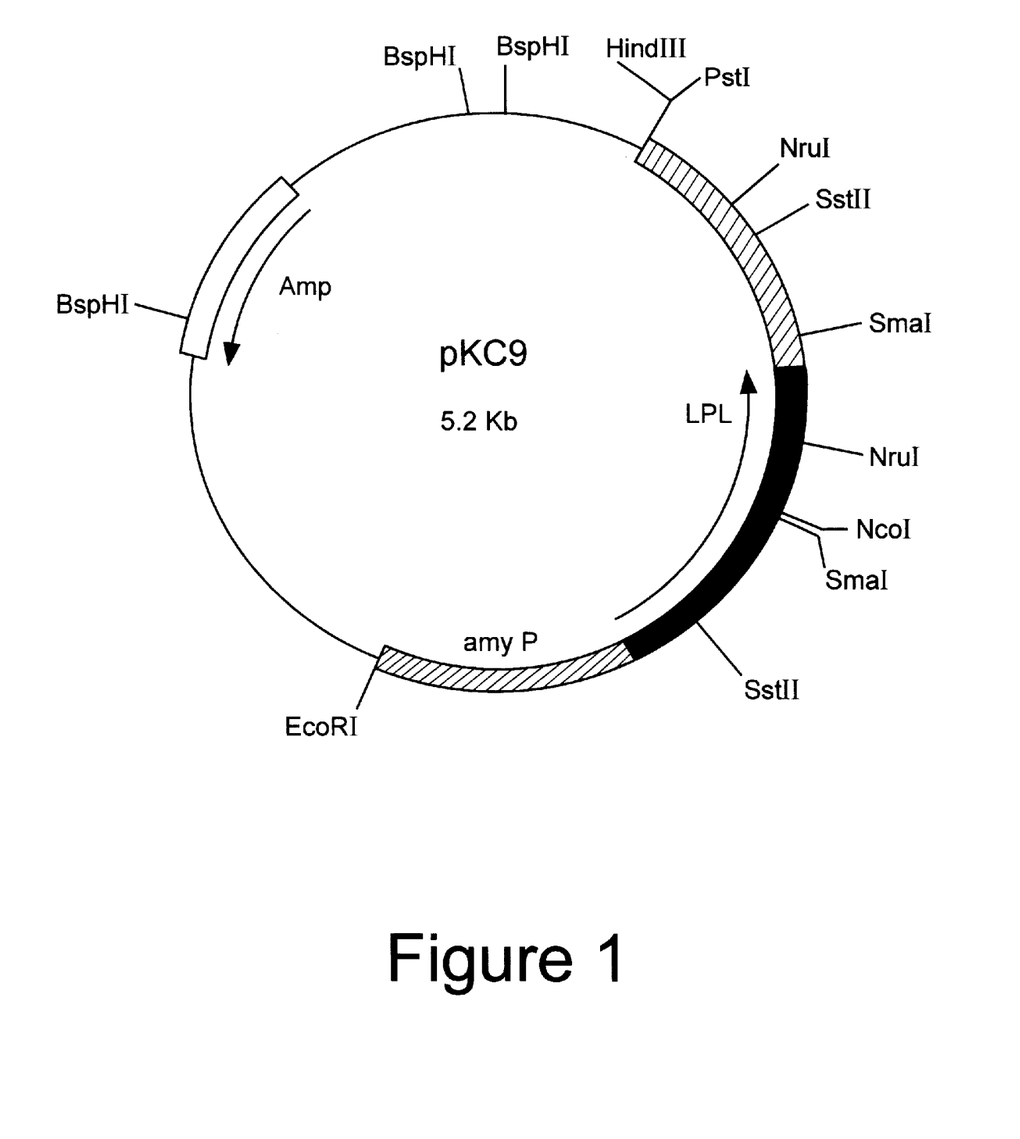
FIG. 1 shows the plasmid map of vector pKC9.
Figure 2:
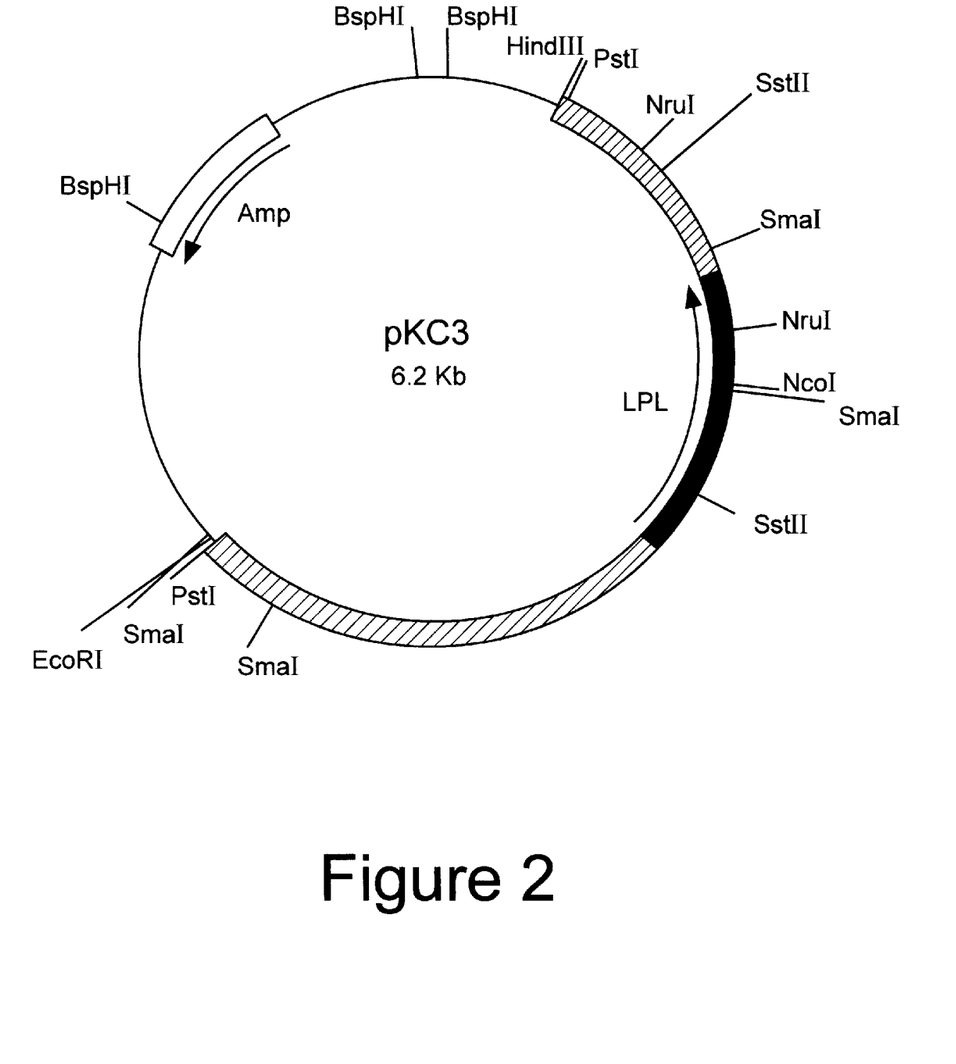
FIG. 2 shows the plasmid map of vector pKC3.
Figure 3:
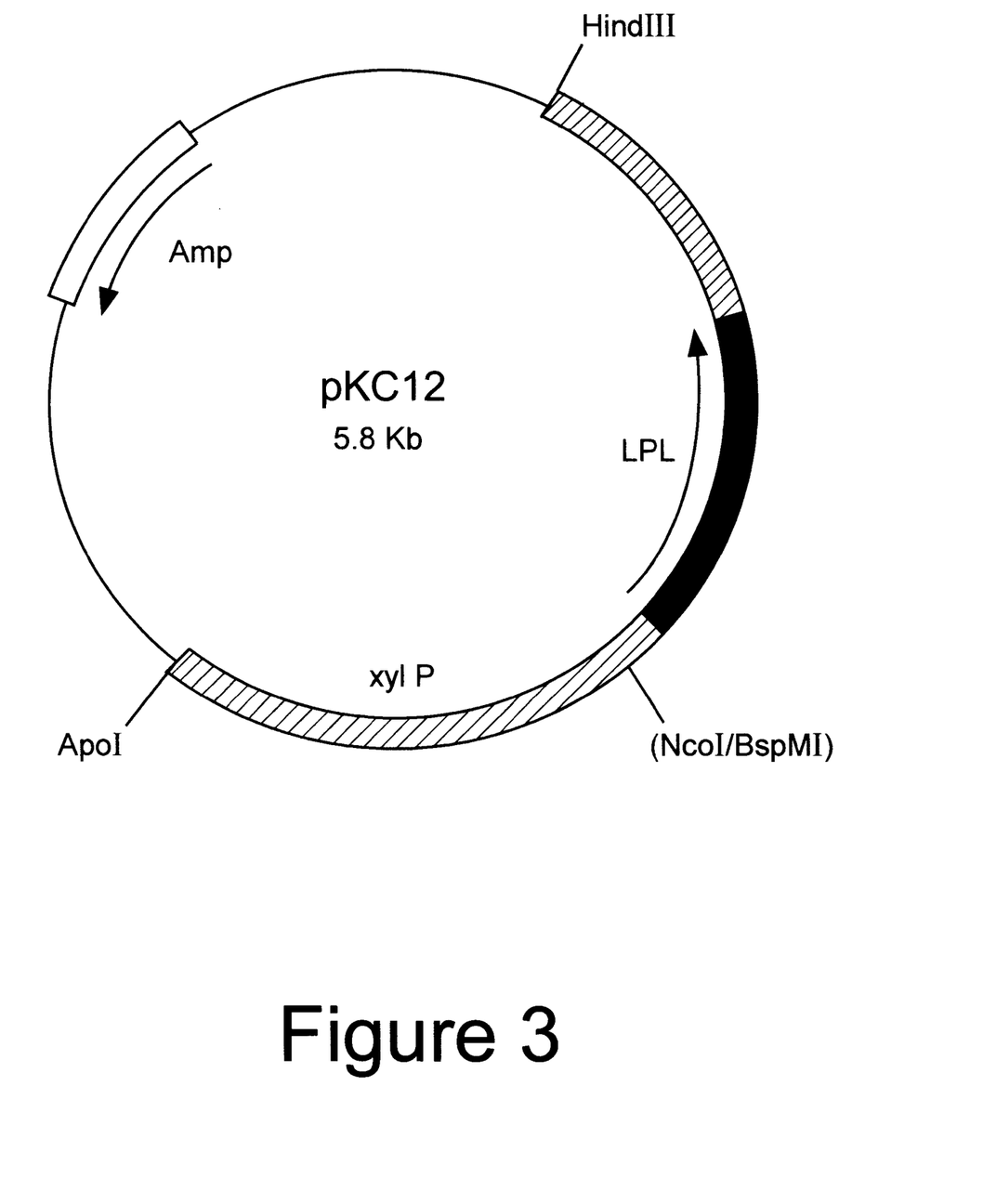
FIG. 3 shows the plasmid map of vector pKC12.

One vector according to the invention is, for example, plasmid pKC3 (c.f. FIG. 2). The plasmid consists of the generally known E. coli plasmid pUC19 together with a HindIII/EcoRI restriction fragment from the chromosomal DNA of A. foetidus RH 3046. The restriction fragment contains the structural gene of LPL with the natural DNA sequence coding for the signal peptide together with the natural 5' promoter sequence upstream from the gene and the natural 3' termination sequence downstream from the gene. The DNA sequences lying upstream and downstream from the structural gene, including the signal peptide sequence, are functional and give rise to expression and secretion in filamentous fungi of the genus Aspergillus, for example in strains of A. foetidus, A. niger, A. phoenicis, A. oryzae or A. sojae.

The person skilled in the art is sufficiently familiar with methods by means of which a gene may be combined in a vector with functional DNA sequences, for example another promoter or a signal peptide sequence (c.f. for example Maniatis et al., (1982), Molecular Cloning, A Laboratory Manual, Cold Spring Harbor Laboratory, New York). The nucleotide sequence for the mature LPL gene or a nucleotide sequence derived therefrom may thus also be associated with functional sequences suitable for expressing and secreting LPL in a filamentous fungus of the genus Aspergillus or in T. reesei other than those present in pKC3, pKC9 or pKC12.

It is especially functional promoter sequences which are of particular significance for the level of expression. These are DNA sequences of approx. 500 to 2000 base pairs in length located 5' upstream from the start codon of an Aspergillus or T. reesei gene.

Such DNA sequences may be isolated, for example, as restriction fragments and ligated with restriction fragments of the LPL gene including the signal peptide sequence. In doing this, incompatible restriction sites or regions without suitable restriction sites may be bridged or replaced, for example with synthetically produced oligonucleotides, such that the original DNA sequence is retained. In this way, the DNA sequence of the LPL gene including the signal peptide may be retained unchanged and functionally associated with a promoter sequence which, itself, is also unchanged.

In order to increase expression, the natural promoter may be replaced with another one. Numerous suitable promoters are known. For example, the TAKA-amylase promoter from A. oryzae (c.f. EP 0 238 023) is suitable for expression in A. oryzae or A. sojae strains, the gpdA promoter from A. nidulans (Punt et al. (1987), Gene 56, pp. 117–124) is suitable for expression in A. nidulans, A. niger, A. phoenicis, A. japonicus, A. foetidus or A. awamori strains. The cbh1 promoter from T. reesei (EP-A-0 244 234) is suitable, for example, for expression in a T. reesei strain.

The natural chromosomal terminator sequence according to SEQ ID NO:1 downstream from the structural gene is preferred as the terminator. Depending upon the strain used for expression or the promoter sequence used, it may be advantageous additionally to exchange the natural leader sequence or also the termination sequence, in order still further to improve expression and secretion. Suitable sequences are, for example, the trpC terminator from A. nidulans (Punt et al., loc. cit.) or the pectinesterase terminator from A. niger (EP 0 388 593).

Transformed Aspergillus or Trichoderma strains for the large scale industrial production of LPL The plasmids according to the invention may be used in the transformation of Aspergillus or Trichoderma reesei strains. Multiple incorporation of the plasmids into the genome of the host strains may occur. By increasing the number of copies of the gene and/or additionally using stronger promoters, it is possible significantly to increase LPL productivity. Those transformants exhibiting particularly high productivity may be selected from a plurality of transformants. Raising LPL productivity simultaneously causes secondary activities, such as unwanted glucoamylase activity, to recede into the background. Strains transformed according to the invention are thus particularly suitable for the large scale industrial production of LPL enzyme products.

Fungal strains of species known to have good enzyme production characteristics are particularly suitable for the expression and secretion of LPL. Particularly preferred strains are those of the species A. niger, A. awamori, A. phoenicis, A. japonicus, A. foetidus, A. oryzae or A. sojae and T. reesi. Suitable strains may be obtained from publically accessible culture collections, such as for example the ATCC, DSM, CBS or NRRL. Suitable host strains are, for example, in particular A. awamori ATCC 11360, A. foetidus ATCC 10254 and ATCC 11359, A. japonicus 16873, A. oryzae NRRL 695, A. niger ATCC 10864, A. phoenicis CBS 136.52 and T. reesel ATCC 26921. A. sojae DSM 10090 is particularly suitable. The gene donor strain A. foetidus RH 3046 is also particularly suitable (c.f. page 3).

The fungal strains may be transformed using known methods. EP 0 184 438 (U.S. Pat. No. 4,885,249) describes, for example, a method for transforming A. niger, in which the argB gene from A. nidulans is used as a selection marker.

Example 9 of EP 0 238 023 describes a generally applicable method for transforming *A. oryzae* strains. In this method, plasmid p3SR2 is used with the amdS gene from *A. nidulans* as a selection marker. EP 0 244 234 describes the transformation of *T. reesei* with this vector. Kelly & Hynes (1985), *EMBO Journal* 4, pp. 475–479 describe the transformation of *A. niger* with p3SR2. Vector pAN7-1 (Punt et al. (1987), *Gene* 56, pp. 117–124) may preferably be used for strains of the species *A. niger, A. awamori, A. japonicus, A. phoenicis* and *A. foetidus*. Transformants may then be selected by their resistance to hygromycin B.

A third selection principle is used for transforming *A. sojae* as the strains used of this species both metabolise acetamide and are resistant to hygromycin B. Selection on a nutrient medium containing chlorine isolates mutants having a defective nitrate reductase (niaD) gene, i.e. which no longer grow using nitrate as the sole source of nitrogen (Cove, D. J. (1976) *Heredity* 36, 191–203). Transformation with plasmid pSTA10 (Unkles, S. E. et al. (1989) *Mol. Gen. Genet.* 218, 99–104), which contains the intact information for the nitrate reductase gene, remedies the defect, such that the transformants grow with nitrate as the sole source of nitrogen, while the growth of the untransformed cells is retarded.

In order to perform transformation, protoplasts are initially produced from vegetative cells or also from conidiospores by enzyme action in an osmotically stabilised medium. Conventionally after two or more washing stages, the plasmid DNA to be transformed is added to this medium in the presence of polyethylene glycol (PEG) and $CaCl_2$, which results in uptake of DNA into the cells. After transformation, the protoplasts are regenerated on an osmotically stabilised medium, whereby selection is performed for those cells having taken up a marker gene.

The fungal strains are preferably transformed using the co-transformation method, in which a plasmid having a selection marker for Aspergillus or *T. reesei* strains and a vector according to the invention (a phage DNA or a cosmid DNA or preferably a plasmid containing the LPL gene) are simultaneously added to the cells to be transformed.

*A. sojae* DSM 10090 may be co-transformed, for example, with plasmids pSTA10 and pKC9. Nitrate-metabolising transformants may then be selected.

From among all the transformants obtained, those having increased or particularly high LPL productivity must then be selected. This selection may be made, for example, on the basis of the LPL productivity of the transformants in shaken flasks.

Process for the Production of LPL with a Host Organism Transformed According to the Invention The transformed host strain may be incubated in a submerged culture in a suitable medium. Suitable media are those in which filamentous fungi exhibit good growth, in particular those simultaneously resulting in good formation of LPL. Very suitable media are those in which the particular Aspergillus or *T. reesei* host strain are known to exhibit good growth and simultaneously form LPL. It is also particularly favourable with regard to low-cost media to use cheap natural products as constituents of the nutrient media, such as for example corn steep solids or corn steep liquor, rye bran, wheat bran, potato dextrin, maltodextrin, potato protein, molasses etc. It is also favourable to use ammonium salts as N sources, for example ammonium sulphate.

The person skilled in the art may be guided by known media for the fermentation of Aspergillus or *Trichoderima reesei* strains and identify particularly suitable media by testing. A suitable medium may, for example, contain 5% maltodextrin and 3% corn steep solids in tap water.

The LPL may be produced by submerged fermentation. Inoculation may here conventionally be achieved by means of an inoculation series from a culture tube or Petri dish culture, via shaken flasks, optionally one or more pre-fermenters into a main fermenter. A conventional duration of fermentation is approx. 30 to 120 hours at approx. 28° C. under aerobic conditions. Upon termination of fermentation, the cell material is separated, for example by filtration, and the culture liquor containing LPL harvested and purified. The culture liquor may be further processed to yield liquid or dry LPL products, for example by ultrafiltration, spray drying or spray pelletisation. In this manner, it is possible to produce LPL enzyme products which are suitable for hydrolysing lysophosphatides.

Use of the LPL Enzyme Product According to the Invention

The hydrolysis reaction is best performed in 5 to 24 hours with stirring within the temperature range from 20 to 65° C., preferably from 35 to 55° C. The starting syrup is conveniently used as a slurry or solution having a solids content of 5 to 35 wt. %. The pH value is generally within the range of from 4 to 5, preferably 4.5.

The process is preferably performed in a single stage by allowing the LPL to act. It is convenient to use 250 to 800 units of LPL per kg of syrup dry matter. The use of recombinant LPL allows substantially higher flow rates to be achieved than is possible, for example, with the conventional LPL described in EP 0 219 269.

The enzyme LPL is conventionally inactivated by pasteurising the syrup.

The following Examples illustrate the invention in greater detail.

EXAMPLES (Unless otherwise stated, percentages in the Examples are weight percentages.)

Example 1

Purification of LPL from *A. foetidus*

1500 ml of culture retentate from A. foetidus PH 3046 were deionised through a Sephadex G25 column (Pharmacia) in order to reduce the electrical conductivity thereof, and rebuffered in buffer A (20 mM tris-HCl, pH 7.0+5 mM Ca acetate). The collected enzyme solution had a conductivity of 3.5 mS/cm.

In a further stage, ion exchange chromatography was performed on DEAE Fractogel (Merck). To this end, 2440 ml of the rebuffered, deionised enzyme solution are introduced in several (9) portions into a DEAE Fractogel column (height 235 mm, diameter 50 mm). The column was rinsed with buffer A. Elution was performed over a continuous gradient from buffer A to buffer B (buffer A+1M NaCl). Elution was performed at an elution rate of 12 ml/min and 18 ml fractions were collected.

The fractions were tested for the presence of LPL. This was achieved by measuring LPL. activity. One LPL unit is here defined as the quantity of enzyme which, in a 0.010 molar aqueous solution of lysolecithin at pH 4.5 and 55° C., results in a hydrolysis rate of 1 micromol per minute.

LPL activity was measured as follows: 0.1 ml of enzyme solution was added to 0.5 ml of substrate solution preheated to 55° C. (0.01M lysolecithin, Sigma order no. L4129, in 0.01M Na acetate buffer, pH 4.5). After a reaction time of 1 minute and after a reaction time of 10 minutes at 55° C., a 0.1 ml portion of this batch was added to 1 ml of reaction mixture A preheated (5 min) to 37° C. (test from Boehringer Mannheim, "Free fatty acids, semi-micro test", order no. 1383175; reaction mixture A contains 11 ml of K phosphate buffer, pH 7.8, tribromohydroxybenzoic acid, Mg chloride and stabilisers, together with a tablet containing ATP, CoA, acyl-CoA synthetase, peroxidase, ascorbate oxidase, 4-aminoantipyrine and stabilisers) and incubated for 5 minutes at 37° C. 0.1 ml of a mixture prepared from 0.55 ml of N-ethylmaleimide solution (contained in test kit) and 0.55 ml of reaction mixture B (contained in Boehringer test kit, 0.6 ml ACOD dilution solution, stabilised, together with a tablet of acyl-CoA oxidase) was added to the above batch and incubated at 3° C. for 5 minutes. The batch is cooled to room temperature in a water bath and optical density at 546 nm determined in a photometer (1 ml cuvettes). The enzyme solution was diluted with distilled water in such a manner that optical density values in the range of 0.5 were obtained. The content of LPL was calculated using the following formula.

Calculation:

$$\frac{E\text{(after 10 min)} - E\text{(after 1 min)} \cdot 1.2 \text{ ml} \cdot 0.6 \text{ ml}}{9 \text{ min} \cdot 16.772 \cdot 1 \text{ cm} \cdot 0.1 \text{ ml} \cdot 0.1 \text{ ml} \cdot \text{enzyme conc. g/ml}}$$

Unit: U/g LPL 16.772=OD of 1 mM palmitic acid, measured in accordance with the above-stated test Analysis volume=1.2 ml Volume of enzyme solution=0.1 ml Volume of free fatty acid=0.1 ml Enzyme concentration=dilution of enzyme solution initial weight of enzyme (g/ml)

Reaction time $t_{min}$=9 (10−1) min

Pathlength of measuring cuvette=1 cm

Volume of buffer+substrate+enzyme=0.6 ml LPL began to elute at approx. 0.1M NaCl. The fractions containing LPL from several runs were combined, dialysed against distilled H$_2$O and then lyophilised. The lyophilisate was dispersed in 168 ml of buffer A. In the next stage, 168 1 ml portions of the samples were introduced into a Mono Q (Pharmacia, 10 ml) anion exchange chromatography column and again eluted in a continuous gradient from buffer A to buffer B. The majority of LPL eluted at between 180 and 210 mmol of NaCl. The eluate, 4035 ml, was dialysed against distilled H$_2$O and then lyophilised.

The lyophilisate was dispersed in 100 ml of buffer A and further purified by gel chromatography in five 20 ml runs through a Sephacryl S-200 HR (Pharmacia) column (770 mm 50 mm).

The fractions containing LPL (300 ml) were combined and mixed with 300 ml of 3.4M ammonium sulphate solution and separated in fifteen 40 ml runs through a phenyl Sepharose [column] (Pharmacia, EF, 83 mm 10 mm), rewashed with 1.7M ammonium sulphate solution in buffer A (buffer C) and eluted with a continuous gradient of buffer C and buffer A. The fractions containing LPL (85 ml) were combined; specific activity was approx. 72 LPL units/mg of protein.

Final Purification of LPL by HPLC

Final purification was performed by reversed-phase chromatography (HPLC) on Nucleosil 500-5 C3 PPN (standard preparation separating column, Macherey & Nagel). 1350 μl portions of the fractions containing LPL were introduced. Elution was performed with an ammonium formate buffer system (buffer A: 10 mM ammonium formate, pH 7.5 (95%), acetonitrile (5%) and buffer B: 100 mM ammonium formate, pH 7.5 (5%), acetonitrile (95%), 9 to 10, up to 80% buffer B. LPL eluted at approx. 47% buffer B.

When subjected to SDS gel electrophoresis, the purified protein exhibits a uniform band having a molecular weight of approx. 37000 Dalton. The isoelectric point is at approx. pH 4.2. The protein purified in this manner was used for sequencing.

Example 2

Partial Amino Acid Sequencing

Starting from the purified enzyme, after cleavage with endoproteinase Asp-N, the peptides were separated by reversed-phase HPLC chromatography. The N-terminal sequence of the native protein and the sequence of the prepared peptides were determined using a gas phase sequenator (Applied Biosystems Model 470A).

The N-terminal amino acid sequence [SEQ ID NO:8] is:

```
Ser-Val-Ser-Thr-Ser-Thr-Leu-Asp-Glu-Leu-Gln-Leu-Phe-Ala-
Gln-Trp-Ser-Ala-Ala-Ala-Tyr-Cys-Ser-Asn-Asn-Ile-Asp-Ser.
```

Peptide Asp-N3, obtained after endoproteinase Asp-N (Boehringer Mannheim) cleavage and having the following amino acid sequence[SEQ ID NO:9 & 10], was used to derive oligonucleotide KC15:

```
Asp-N3:  Glu-His-Ile-Thr-Ser-Gln-Gly-Ser-Gly-Ala-Asn-Phe-
         Arg

KC15:    3'-CTC GTG TAG TGG AGG GTC CCG AGG CGG-5'
```

Example 3

Derivation & Synthesis of DNA Probes

The sequence of the KC13 oligonucleotide was derived from the N-terminal amino acid sequence of the lysophospholipase and altered at the 5' end to encompass the sequence of the oligonucleotide TCCAAGCTT, in order to obtain a HindIII cleavage site.

Oligonucleotide KC13 is a so-called "mixed probe". Its sequence reads:

```
N terminus:  Ser-Thr-Leu-Asp-Glu-Leu-Gln-Leu-Phe-Ala-Gln-

KC13:        5'-TCC AAG CTT GAC GAA CTI CAA CTI TTC GCI CA-3'
                       T   G T     G T     T
             HindIII
```

Oligonucleotide KC15 derived from the peptide fragment Asp-N3 was used to identify the PCR product or for Northern analyses and to identify colonies.

```
KC15: 3'-CTC GTG TAG TGG AGG GTC CCG AGG CGG-5'
```

The nucleotide sequence was synthesised using the phosphoramidite method developed by Beaucage, S. L. and Caruthers, M. H., (1981), *Tetrahedron Letters* 22, pp. 1859–1862 and using a DNA synthesiser (Applied Biosystems 380 A DNA Synthesizer).

Example 4
Preparation of RNA from the Induced Cells

A modified method after Vierula, P. J. and Kapoor, M., (1989), *J. Biol. Chem.* 264, pp. 1108–1114, was used to isolate RNA from *Aspergillus foetidus*.

Example 5
Synthesis of cDNA and Isolation of an LPL-Specific cDNA Clone cDNA synthesis was performed using the method of Russo et al. (1991), *EMBO J.* 10, pp. 563–571. This method is based on the principle of initially transcribing all the polyadenylated RNA molecules into single-stranded cDNA using an oligo(dT) primer (EA13). This cDNA synthesis is followed by a PCR reaction. This reaction is initiated by a sequence-specific primer (KC13). The back reaction proceeds by a partial sequence of the oligo(dT) primer (EA14). Recognition cleavage sites for restriction enzymes are already incorporated in this sequence.

The sequences of the EA13 and EA14 oligonucleotide, respectively, read:

```
EA13: 5'-GAC TCG AGT CGA CAT CGA (T)21 A/C/G-3'

EA14: 5'-GAC TCG AGT CGA CAT CGA TT-3'
         XhoI    SalI
```

Conditions for the Synthesis of the Single-Stranded cDNA

10 μg of total RNA, 50 mM tris-HCl, pH 8.3, 5 mM $MgCl_2$, 75 mM KCl, 5 mM DTT, 0.4 mM dNTP (0.4 mM each of dATP, dCTP, dGTP, dTTP), 30 pmol of EA13 and 200 U of M-MLV reverse transcriptase (Gibco-BRL GmbH, 7514 Eggenstein, FRG) were used to synthesise the first strand in a reaction volume of 50 μl. Incubation was performed for 45 minutes at 42° C.

Test Conditions for the PCR Reaction 20 mM tris-HCl, pH 8.4, 50 mM KCl, 1.5 mM $MgCl_2$, 0.2 mM dNTP (0.2 mM each of dATP, dCTP, dGTP, dTTP), 70, pmol of EA14, 77 pmol of KC13, 2 μl from the first strand cDNA synthesis reaction batch and 5 U of Taq-DNA polymerase (Gibco-BRL) were used for the polymerase chain reaction in a reaction volume of 100 μl. The batch was passed through 20 cycles (94° C., 40 sec; 50° C., 2 min; 72° C., 3 min).

Once the PCR products had been separated by gel electrophoresis, it was possible to identify a fragment of approx. 0.9 kb which hybridised with oligonucleotide KC15. The PCR products were precipitated with ethanol, cleaved with HindIII/SalI and inserted into plasmid pUC18.

195 white colonies were obtained. 48 of these colonies were selected and a rapid plasmid preparation performed. After hybridisation with oligo-KC15, nine colonies designated pKC1/a no. 5, 16, 17, 22, 21, 30, 36, 43 and 46 exhibited clear signals. The plasmids of clones no. 5 and 36 were prepared and sequenced.

The amino acid sequence derived from the nucleotide sequence corresponds with the sequence determined by Edman degradation.

Plasmid pKC1/36, however, contained only the nucleotide and amino acid sequence of the lysophospholipase cDNA from codon 29. In order to obtain precise information about the signal sequence and also about the intron/exon distribution in the genomic DNA, the entire cDNA gene was cloned by means of the PCR method. Isolation of the RNA, synthesis of the single-stranded cDNA and the conditions for the polymerase chain reaction were identical to those used previously for cloning plasmid pKC1/36. One change was, however, to use oligonucleotide KC24 instead of oligonucleotide KC13 as the primer in the polymerase chain reaction. Oligonucleotide KC24 was derived from the genomic lysophospholipase gene and is located starting from nucleotide −50 upstream from the start codon ATG. The sequence (KC24) reads: 5'-GTT GGT CGC AAG GTT TTG-3'.

The PCR product was cleaved with AccI and inserted into plasmid pUC18, which had been cleaved with the same enzyme. The HindIII/SalI fragment of plasmid pKC1/36 was used as a gene probe to identify colonies. The new recombinant plasmid with the designation pKC/ATG was sequenced. The sequence of the insertion is shown in SEQ ID NO:1.

Example 6
Isolation of Chromosomal Lysophospholipase Gene

The chromosomal lysophospholipase gene was isolated by direct cloning of the chromosomal DNA hydrolysed with restriction enzymes into vector pUC18. First of all, the chromosomal DNA was isolated from *A. foetidus* RH 3046, fragmented with restriction enzymes and characterised by Southern analysis. The HindIII/SalI fragment from plasmid pKC1/36 was used as the hybridisation probe. On the basis of the result from the Southern hybridisation, the chromosomal DNA of *A. foetidus* RH 3046 was completely hydrolysed with BamHI and fractionated by size in a sucrose gradient. Fractions containing DNA fragments of a size of approx. 9 to 10 kb were collected, precipitated with ethanol and inserted into plasmid pUC18, which had been cleaved with BamHI. 1904 recombinant clones were obtained. Of these, 24 positive transformants could be identified by colony hybridisation. The plasmid DNA of transformant no. 1 and no. 3 was isolated, mapped, hybridised again and the zones of the gene corresponding to the N- and C-terminal regions of the protein were then sequenced. The result confirmed that both clones contain the chromosomal lysophospholipase gene. This new plasmid is designated pKC6.

Since plasmid pKC6 contained a very large 5' and 3' untranslated region, the PstI fragment from plasmid pKC6 was isolated and inserted into plasmid pUC18 which had been cleaved with PstI. The new plasmid was designated pKC3. The entire insertion sequence of plasmid pKC3 is shown in SEQ ID NO:1. By comparing the genomic DNA with the lysophospholipase cDNA, it was possible to identify additional 1608 nucleotides upstream from the ATG in the genomic DNA, such that both the cDNA sequence and the genomic sequence of the lysophospholipase structural gene was determined. The genomic gene contains three introns. The 3' non-coding region comprises 997 nucleotides. The signal sequence determined by computer analysis contains 21 amino acids. The lysophospholipase gene is probably synthesised as preprotein, with the propeptide comprising six amino acids.

Example 7
Construction of Expression Vector pKC9

Vector pKC9 contains the genomic lysophospholipase gene and the *Aspergillus oryzae* α-amylase promoter from plasmid pK54. In order to place the α-amylase promoter upstream from the lysophospholipase gene, the initiation sequence TA TAC CGC AAG ATG TTC had to be replaced with the sequence AC CTG CTA ACC ATC TTC, which contains the recognition sequence for BspMI. The polymerase chain reaction (PCR) was used for this purpose. Two oligonucleotide primers having the following sequences were used:

```
KC29:   5'-GGA ATT CAC CTG CTA ACC ATG TTC TCT GGA CGG TTT GGA GTG-3'
                    BspMI

SupI:   5'-CGC CAG GGT TTT CCC AGT CAC GAC-3'
```

20 mM tris-HCl, pH 8.4, 50 mM KCl, 1.5 mM MgCl, 0.2 mM dNTP (0.2 mM each of dATP, dCTP, dGTP, dTTP), 50 pmol of each of KC29 and SupI, 1 ng of pKC3 as matrix and 2.5 U of Taq polymerase (Perkin-Elmer) were mixed in a reaction volume of 100 μl for the polymerase chain reaction. The batch was passed through 20 cycles (94° C., 40 sec; 40° C., 2 min; 72° C., 2 min). On completion of the reaction, the amplified fragment was purified, hydrolysed with BspMI and HindIII and inserted into plasmid pK54, which had been cleaved with NcoI/HindIII. The structure of plasmid pKC9 was confirmed by restriction analysis and subsequent sequencing.

Construction of Expression Vector pKC12

The lysophospholipase gene was used in plasmid pKC12 under the control of the *Aspergillus niger* xylanase promoter. The structure of plasmid pKC12 was identified in the same manner as that of plasmid pKC9. On completion of the polymerase chain reaction (PCR), the amplified fragment containing the lysophospholipase gene was hydrolysed with BspMI and HindIII and inserted into plasmid pxylP, which had been cut with NcoI/HindIII and contains the *Aspergillus niger* xylanase promoter.

The structure of plasmid pKC12 was confirmed by restriction analysis and subsequent sequencing.

Example 8

Transformation Method for Aspergillus and *Trichoderma reesei* strains

A spore suspension of the fungal strain to be transformed was prepared from an approx. 2 week old Petri dish culture in approx. 10 ml of 0.85% NaCl by spatula-assisted floatation. Four 1 litre shaken flasks containing 100 ml of Czapek-Dox minimal medium (Oxoid) with 0.1% yeast extract were each inoculated with 1 ml of spore suspension and incubated for approx. 16 hours at 28° C. on a rotary shaker and 120 rpm. The mycelium from each of the four shaken flasks was harvested by means of a filter paper and rinsed with approx. 50 ml of MP buffer (1.2 mM MgSO$_4$ in 10 mM phosphate buffer, pH 5.8). Once the buffer had drained away, the moist mycelium was weighed. Approx. 3 to 5 g of moist mycelium were generally obtained.

5 ml of MP buffer, 120 μl of Novozym solution (1 g of Novozym® 234 (Novo Nordisk) in 6 ml of MP buffer) and 25 μl of β-glucuronidase (Sigma) were added for each g of moist mycelium. The mycelium suspension was placed in iced water for 5 minutes. 60 μl of bovine serum albumin solution (0.2 g of bovine serum albumin in 4 ml of MP buffer, sterile filtered) were then added and the batch incubated at 30° C. with gentle shaking. Protoplast formation was monitored visually under the microscope. Once no further substantial increase in protoplast formation was observed, the batch was terminated in order to harvest the protoplasts. This generally occurred after approx. 3 to 5 hours.

In order to separate any coarse mycelium constituents still present, the protoplast suspension was passed through a glass wool filter impregnated with MP buffer and transferred into centrifuge tubes. The upper half of the tube was covered with a layer of 600 mM sorbitol, 100 mM tris-HCl, pH 7.0. The tubes were centrifuged for 10 minutes at 2500 g. The protoplasts were removed from the interlayer and dispersed in 1M sorbitol, 10 mM tris-HCl, pH 7.5. The prot-oplasts were then washed twice by centrifugation at 1500 g with STC buffer (1M sorbitol, 10 mM tris-HCl, pH 7.5, 10 mM CaCl$_2$) and finally dispersed in 1 ml of STC buffer.

In order to transform *A. oryzae* or *A. foetidus*, 300 μl of protoplast suspension, approx. 10 μg of p3SR2 as the selection plasmid and 10 μg of the particular plasmid to express the LPL were combined in 25 μl of 10 mM tris-HCl, pH 8.0, and incubated for 10 minutes at 0° C. A further 25 μl of the same DNA amount and 400 μl of PEG solution (60% polyethylene glycol 6000 (Fluka) in 10 mM tris-HCl, pH 7.5, 50 mM CaCl$_2$) were then added, very carefully mixed and incubated for 5 minutes at room temperature. A further 600 μl of PEG solution were added, mixed in and the batch was incubated for a further 20 minutes at room temperature. Approx. 9 ml of acetamide soft agar (minimal medium containing 10 mM acetamide as the sole source of N, 1M sucrose, 0.6 wt. % agar) were mixed into the batch at 45° C. and distributed on four Petri dishes containing the same medium, but with 1.5 wt. % agar (Oxoid) and additionally 15 mM CsCl. The plates were incubated at 28° C. After 6 to 10 days, the rapidly growing colonies (transformants) were isolated on acetamide medium without sucrose, purified twice via single spore colonies and finally transferred onto complete medium, for example potato/dextrose agar.

Strains of the species *A. niger*, *A. awamori*, *A. foetidus*, *A. japonicus* or *A. phoenicis* may also be transformed with plasmid p3SR2. Preferably, however, transformation was performed with plasmid pAN7-1. Preparation of the protoplasts and addition of the plasmid DNA was performed in the same manner as described above for plasmid p3SR2. However, instead of adding acetamide soft agar, the entire transformation batch is added to and carefully mixed with 100 ml of Czapek-Dox minimal medium (Oxoid) containing 100 μg of hygromycin B/ml, 1.5 wt. % of agar (Oxoid) and 1M sucrose, which has been cooled to approx. 45° C. 10 ml portions of the batch are then placed in Petri dishes, into each of which 10 ml of Czapek-Dox minimal medium (Oxoid) containing 1.5 wt. % of Agar (Oxoid), but without hygromycin and without sucrose, had been placed as a solid substrate layer. Once the upper agar layer has solidified, the Petri dishes are incubated at 37° C. Hygromycin B resistant transformants may be subcultured after approx. 3 to 10 days and, in order to verify resistance, transferred onto Czapek-Dox minimal medium (Oxoid) containing 50 μg of hygromycin B/ml and 1.5 wt. % of agar (Oxoid).

A third principle of selection is used for the transformation of *A. sojae* as the strains used of this species both metabolise acetamide and are resistant to hygromycin B. Selection on a nutrient medium containing chlorine isolates mutants having a detective nitrate reductase (niaD) gene, i.e. which no longer grow using nitrate as the sole source of nitrogen (Cove, D. J. (1976) *Heredity* 36, 191–203). Transformation with plasmid pSTA10 (Unkles, S. E. et al. (1989) *Mol. Gen. Genet.* 218, 99–104), which contains the intact information for the nitrate reductase gene, remedies the defect, such that the transformants grow with nitrate as the sole source of nitrogen, while the growth of the untransformed cells is retarded.

Example 9
Production of LPL-Secreting Transformants

Homologous transformation of pKC12 in *A. foetidus* RH 3046

Hygromycin B resistant transformants were isolated from the agar dishes with regeneration medium by co-transformation of *A. foetidus* RH 3046 with the two plasmids pAN7-1 (c.f. Example 8) and pKC12 in the manner described above. Once purity had been verified by plating out, shaking tests were used to test the transformants for LPL production.

250 ml conical flasks containing 40 ml of nutrient solution consisting of

| | |
|---|---|
| maltodextrin | 3.75% |
| corn steep solids | 3% |
| $K_2HPO_4$ | 2% |
| $KH_2PO_4$ | 1.4% |
| tap water, sterilised at 121° C. for 30 minutes, | | are inoculated with spore suspension of the transformants to be tested and shaken for 120 hours at 28° C., 200 rpm and an offset of 25 mm. The cell mass was filtered out and LPL activity was determined in the culture filtrate. Transformant *A. foetidus* RH 3046 pAN7-1 pKC12 no. 40, for example, exhibited a 100% increased LPL activity in the culture filtrate in comparison with the host strain *A. foetidus* RH 3046.

Heterologous transformation of pKC9 in *A. sojae* RH 3782

Strain *A. sojae* RH 3782 niaD22, a mutant of *A. sojae* RH 3782 produced according to Cove (1976), is cultured in the following nutrient solution prepared from

| | |
|---|---|
| glucose (Merck) | 2% |
| malt extract (Oxoid) | 0.5% |
| Bacto-peptone (Difco) | 0.025% |
| deionised water | |
| adjust pH to 5.0; sterilisation: 30 min at 121° C. | |

Protoplasts are obtained from the mycelium using the method described in Example 8 and, with pSTA10 as the selection plasmid, are co-transformed in each case with one of the plasmids pKC3, pKC9 or pKC12. The protoplasts are regenerated by mixing the transformation batch with 9 ml of (osmotically stabilising) soft agar consisting of

| | |
|---|---|
| 0.1M Na phosphate buffer, pH 6.0 | 15 ml |
| 1M sucrose (Merck) | 10.28 g |
| Millipore water to make up to | 29.1 ml |
| agar (Oxoid) | 0.18 g (= 0.6%) |
| 30 min sterilisation at 121° C., then sterile addition of: | |
| salt solution (7.14.2) | 0.6 ml |
| 1M $NaNO_3$ solution | 0.3 ml | and distributed on four agar plates of the same composition but prepared using 1% agar. After approx. 6 to 10 days' incubation at 37° C., the transformants are isolated from the agar plates and purified by plating out on nitrate/sucrose agar. Numerous transformants were obtained by selection and subsequent purification on a nutrient medium containing nitrate as the sole source of N and tested for LPL production in shaken flasks using the following nutrient solution.

| | |
|---|---|
| maltodextrin | 3.75% |
| corn steep solids | 3.0% |
| $KH_2PO_4$ | 1.0% |
| $K_2HPO_4$ | 0.7% |
| Triton X-100 | 1.0% |
| in tap water, sterilised at 121° C. for 30 minutes. | |

In addition to transformants producing no or only small quantities of LPL (such as the untransformed host *A. sojae* RH 3782 or *A. sojae* RH 3782 niaD22), other transformants are also found which exhibit distinctly increased LPL activity in the culture filtrate. These strains, designated co-transformants, are suitable for producing the enzyme.

| Strain or transformant activity | relative LPL |
|---|---|
| *A. sojae* RH 3782 niaD22 | 100 |
| *A. sojae* RH 3782 niaD22 pSTA10 pKC3 | 230 |
| *A. sojae* RH 3782 niaD22 pSTA10 pKC9 | 320 |
| *A. sojae* RH 3782 niaD22 pSTA10 pKC12 | 220 |

We claim:

1. A recombinant deoxyribonucleic acid (DNA) isolated from Aspergillus, wherein said DNA codes for lysophospholipase (LPL) and has the nucleotide sequence for mature LPL stated in SEQ ID NO: 1.

2. A recombinant deoxyribonucleic acid as claimed in claim 1, wherein said DNA is isolated from *Aspergillus foetidus*.

3. A vector containing a) DNA sequences to replicate the vector in *E. coli*, b) DNA sequences to express and secrete a polypeptide in an Aspergillus strain or a *Trichoderm reesei* strain which code for a promoter, a signal peptide sequence and optionally for a terminator,     c) a polypeptide-coding DNA sequence which is functionally associated with the DNA sequences according to (b),     wherein the DNA sequence according to c) has a nucleotide sequence corresponding to the nucleotide sequence for mature LPL stated in SEQ ID NO:1.

4. A vector as claimed in claim 3, wherein the vector is a plasmid.

5. A vector as claimed in claim 4, wherein the vector is plasmid pKC3, pKC9 or pKC12.

6. A vector as claimed in claim 3, wherein the vector is a phage or a cosmid.

7. A vector as claimed in claim 3, wherein the DNA sequences according to b), which code for a promoter, are selected from the group comprising TAKA-amylase A promoter, gpdA promoter from *Aspergillus nidulans*, pectinesterase promoter from *Aspergillus niger*, polygalacturonidase promoter from *Aspergillus niger*, glucoamylase promoter from *Aspergillus niger* or *Aspergillus awamori*, xylanase promoter from *Aspergillus foetidus*, lysophospholipase promoter from *Aspergillus foetidus*, cellobiohydrolase (cbh 1) promoter from *Trichoderma reesei*.

8. A vector as claimed in claim 3, wherein the DNA sequences according to b), which code for a signal peptide sequence, are selected from the group comprising TAKA-amylase A signal peptide sequence, pectinesterase signal peptide sequence from *Aspergillus niger*, polygalacturonidase signal peptide sequence from *Aspergillus niger*, glucoamylase signal peptide sequence from *Aspergillus niger* or *Aspergillus awamori*, xylanase signal peptide sequence from *Aspergillus foetidus*, lysophospholipase signal peptide sequence from *Aspergillus foetidus*, cellobiohydrolase signal peptide sequence (cbh 1) from *Trichoderma reesei*.

9. A transformed host organism for the production of lysophospholipase, wherein the host organism is an Aspergillus strain or a *Trichoderma reesei* strain and is transformed with a vector as claimed in claim 3.

10. A transformed host organism as claimed in claim 9, wherein the host organism is a strain of *Aspergillus niger, Aspergillus awamori, Aspergillus foetidus, Aspergillus japonicus, Aspergillus phoenicis, Aspergillus oryzae, Aspergillus sojae* or *Trichoderma reesei*.

11. A transformed host organism as claimed in claim 10, wherein the host organism is *Aspergillus niger* ATCC 10864, *Aspergillus awamori* NRRL 3112, *Aspergillus awarmori* ATCC 11360, *Aspergillus foetidus* RH 3046, *Aspergillus foetidus* ATCC 11359, *Aspergillus japonicus* ATCC 16873, *Aspergillus phoenicis* CBS 136.52, *Aspergillus oryzae* NRRL 695, *Aspergillus sojae* RH 3782 or *Trichoderma reesei* ATCC 26921.

12. A process for the production of lysophospholipase by fermentation of a transformed host organism in a suitable culture medium and isolation of the lysophospholipase from the cell-free culture filtrate, wherein the transformed host organism is an Aspergillus strain or a *Trichoderma reesei* strain and has been transformed with a vector as claimed in claim 3.

13. A process as claimed in claim 12, wherein the transformed host organism is a strain of *Aspergillus niger, Aspergillus awamori, Aspergillus foetidus, Aspergillus japonicus, Aspergillus phoenicis, Aspergillus oryzae, Aspergillus sojae* or *Trichoderma reesel*.

14. A process as claimed in claim 12, wherein the transformed host organism is a transformant of *Aspergillus niger* ATCC 10864, *Aspergillus awamori* NRRL 3112, *Aspergillus awamori* ATCC 11360, *Aspergillus foetidus* RH 3046, *Aspergillus foetidus* ATCC 11359, *Aspergillus japonicus* ATCC 16873, *Aspergillus phoenicis* CBS 136.52, *Aspergillus oryzae* NRRL 695, *Aspergillus sojae* RH 3782 or *Trichoderma reesei* ATCC 26921.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 3650 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: intron
        (B) LOCATION: 1691..1743

(ix) FEATURE:
        (A) NAME/KEY: intron
        (B) LOCATION: 1910..1954

(ix) FEATURE:
        (A) NAME/KEY: intron
        (B) LOCATION: 2292..2344

(ix) FEATURE:
        (A) NAME/KEY: CDS
        (B) LOCATION: join(1609..1690, 1744..1909, 1955..2291, 2345
            ..2650)

(ix) FEATURE:
        (A) NAME/KEY: mat_peptide
        (B) LOCATION: 1690..2650

(ix) FEATURE:
        (A) NAME/KEY: sig_peptide
        (B) LOCATION: 1609..1689

(ix) FEATURE:
        (A) NAME/KEY: misc_feature
        (B) LOCATION: 2387..2425
        (D) OTHER INFORMATION: /product= "probe KC15"

(ix) FEATURE:
        (A) NAME/KEY: misc_feature
        (B) LOCATION: 1563..1580
        (D) OTHER INFORMATION: /product= "oligonucleotide KC24"

(xi) SEQUENCE DESCRIPTION: SEQ ID NO:1:

```
CTGCAGATCA CAAGCCGGAC TGATTTTGAA CCGATTGATT GATTGAACCG CCGAAAAGTC    60

TGAAGAATCC TTCAATCCCA ACCAACACGC ACACACACAC GGTATGGATT GGAAGAAAGG   120

AAGGAAGGGA GAAAGTGGGG TTACCCAAGT AAACCGGCAA ACAGACTAAC AAACTCGCAA   180

GGAAGTTAAC TAACTAGTAA TAATATTATG AAGTGAAGGG AGTCACCTCA CCGTCTTCCC   240

GTCCCCTAAC AAACTAACTA GTTAACTACC CCGGGGTTAG TTATAGTACG GGATACTAAG   300

GCATGCACCC CGCAGCCCGG GAAGCCCGGA CGTTTGTTGT TGGTGGTTGT GACTACGGAG   360

TACTAGTCCA GTAGGGGACT CGTAAGGCAG CGGGACTAAT TAACTAGTTC GTTATTTAGG   420

CTGCCAAAGT AAATACCTAG TGCTGTGTGG GTGGTGTAAG TGCCGGGATG AAGTGAGGAG   480

TTTAGTTTTA GGTGAGTGAA TAATAACTTT CAGGTAACTA GGTAATGGAT TGACTTAGTA   540

GTTGAGTGGT TACTATCGTA GTAGACTTGG TTAGGTAATG AGAGATTTCT TTACTATAAC   600

TAGGTTATTT GTTGTATTAC TATCCTAAAA CTGTGAGAGT TCTTGGGAAG GTAAGGTAGT   660

ATTGGGGCC GGGAATAAGG GATGAGTATT GTTTCAATAG TGAGTTGAGG TATTTTCTTT   720

TTCTATTTTC TTTTTGTCAA AGTTACTTAC TTCTTCGATA GTATGGTATT GATTATGGGC   780

ACGTGGACAT GTTCAAATTT TCGTAACATA CATAGATTGT TTGTGTGCTT TTTCCCCATC   840

TATAGTATGT ACTATGTATG TATCGTAGTC TGAATGAGTA TAAGCGCTGC AAGTGATCGG   900

CAAAGTGACA AGAAGTCACT AACTCCACTA GTTACTTGCA TGTCACGAAC CACAACCCTT   960

GACAAGCAAC AGCAACAGTA GCAGCATGTG AAGAAGTCTC AGATTTCGTA ACACCATTTC  1020

CCGTTGACTT GCTCTCCGAT TCGGTCTACT TACCTCGGCC TGTGGACATG TCATGGCCCT  1080

ATCCCCAATC TCCATCTCCA TCTCAATCTA CTGCTCATGT GCAGTACCAC GCCCTCCACG  1140
```

-continued

```
TTTCTCCGCC AGTAGATCCT TCGACACCGC CCATTCTCAG ACAACATCTA CTTTATTTAA    1200

CTTTTCGGAG CAGACTATGC TTGTCTAGGC CTGCTATAGC AGCCCGTTAA TCCCCACCGG    1260

GCTTCCGCTC CGGATGGAGA TGGGGCCAAA CTGGCAACTC CAGTTGCGCA ACGGACAACC    1320

GCCGACCCGG AACAAAGGAT GCGGATGAGG AGATACGGTG CCTGATTGCA TGGCTGGCTT    1380

CATCTGCTAT CGTGACAGTG CTCTTTGGGT GAATATTGTT GTCTGACTTA CCCCGCTTCT    1440

TGCTTTTTCC CCCCTGAGGC CCCTGATGGG GAATCGCGGT GGGTAATATG ATATGGGTAT    1500

AAAAGGGAGA TCAGAGGTGC AGTTGGATTG AGGCAGTGTG TGTGTGTGCA TTGCAGAAGC    1560

CCGTTGGTCG CAAGGTTTTG GTCGCCTCGA TTGTTTGTAT ACCGCAAG ATG TTC TCT    1617
                                                    Met Phe Ser
                                                    -27     -25

GGA CGG TTT GGA GTG CTC TTG ACA GCG CTT GCT GCG CTG GGT GCT GCC    1665
Gly Arg Phe Gly Val Leu Leu Thr Ala Leu Ala Ala Leu Gly Ala Ala
            -20             -15             -10

GCG CCG GCA CCG CTT GCT GTG CGG A GTAGGTGTGC CCGATTTGAG           1710
Ala Pro Ala Pro Leu Ala Val Arg
            -5

GTGGTTGGAT AGCACTGATG AAGGTGTGAA TAG  GT GTC TCG ACT TCC ACG TTG    1763
                                        Ser Val Ser Thr Ser Thr Leu
                                          1               5

GAT GAG TTG CAA TTG TTC GCG CAA TGG TCT GCC GCA GCT TAT TGC TCG    1811
Asp Glu Leu Gln Leu Phe Ala Gln Trp Ser Ala Ala Ala Tyr Cys Ser
        10              15              20

AAT AAT ATC GAC TCG AAA GAC TCC AAC TTG ACA TGC ACG GCC AAC GCC    1859
Asn Asn Ile Asp Ser Lys Asp Ser Asn Leu Thr Cys Thr Ala Asn Ala
    25              30              35

TGT CCA TCA GTC GAG GAG GCC AGT ACC ACA ATG CTG CTG GAG TTC GAC CT  1909
Cys Pro Ser Val Glu Glu Ala Ser Thr Thr Met Leu Leu Glu Phe Asp Leu
40              45              50                  55

GTATGTCACT CAGATCGCAG ACATAGAGCA CAGCTAATTG AACAG G ACG AAC GAC    1964
                                                   Thr Asn Asp
TTT GGA GGC ACA GCC GGT TTC CTG GCC GCG GAC AAC ACC AAC AAG CGG    2012
Phe Gly Gly Thr Ala Gly Phe Leu Ala Ala Asp Asn Thr Asn Lys Arg
60              65              70              75

CTC GTG GTC GCC TTC CGG GGA AGC AGC ACG ATT GAG AAC TGG ATT GCT    2060
Leu Val Val Ala Phe Arg Gly Ser Ser Thr Ile Glu Asn Trp Ile Ala
            80              85              90

AAT CTT GAC TTC ATC CTG GAA GAT AAC GAC GAC CTC TGC ACC GGC TGC    2108
Asn Leu Asp Phe Ile Leu Glu Asp Asn Asp Asp Leu Cys Thr Gly Cys
        95              100             105

AAG GTC CAT ACT GGT TTC TGG AAG GCA TGG GAG TCC GCT GCC GAC GAA    2156
Lys Val His Thr Gly Phe Trp Lys Ala Trp Glu Ser Ala Ala Asp Glu
    110             115             120

CTG ACG AGC AAG ATC AAG TCT GCG ATG AGC ACG TAT TCG GGC TAT ACC    2204
Leu Thr Ser Lys Ile Lys Ser Ala Met Ser Thr Tyr Ser Gly Tyr Thr
125             130             135

CTA TAC TTC ACC GGG CAC AGT TTG GGC GGC GCA TTG GCT ACG CTG GGA    2252
Leu Tyr Phe Thr Gly His Ser Leu Gly Gly Ala Leu Ala Thr Leu Gly
140             145             150             155

GCG ACA GTT TTG CGA AAT GAC GGG TAT AGC GTT GAG CTG GTGAGTCCTT    2301
Ala Thr Val Leu Arg Asn Asp Gly Tyr Ser Val Glu Leu
            160             165

CACAAAGGTG ATGGAGCGAC AATCGGGTTC TGACAGTCAA TAG TAC ACC TAT GGA    2356
                                                Tyr Thr Tyr Gly
                                                        170

TGT CCT CGA ATC GGA AAC TAT GCG CTG GCT GAG CAT ATC ACC AGT CAG    2404
Cys Pro Arg Ile Gly Asn Tyr Ala Leu Ala Glu His Ile Thr Ser Gln
```

```
              175                 180                 185
GGA TCT GGG GCC AAC TTC CGT GTT ACA CAC TTG AAC GAC ATC GTC CCC      2452
Gly Ser Gly Ala Asn Phe Arg Val Thr His Leu Asn Asp Ile Val Pro
    190                 195                 200

CGG GTG CCA CCC ATG GAC TTT GGA TTC AGT CAG CCA AGT CCG GAA TAC      2500
Arg Val Pro Pro Met Asp Phe Gly Phe Ser Gln Pro Ser Pro Glu Tyr
205                 210                 215                 220

TGG ATC ACC AGT GGC AAT GGA GCC AGT GTC ACG GCG TCG GAT ATT GAA      2548
Trp Ile Thr Ser Gly Asn Gly Ala Ser Val Thr Ala Ser Asp Ile Glu
                225                 230                 235

GTC ATC GAG GGA ATC AAT TCA ACG GCG GGA AAT GCA GGC GAA GCA ACG      2596
Val Ile Glu Gly Ile Asn Ser Thr Ala Gly Asn Ala Gly Glu Ala Thr
            240                 245                 250

GTG AGC GTT TTG GCT CAC TTG TGG TAC TTT TTC GCG ATT TCC GAG TGC      2644
Val Ser Val Leu Ala His Leu Trp Tyr Phe Phe Ala Ile Ser Glu Cys
        255                 260                 265

CTG CTA TAACTAGACC GACTGTCAGA TTAGTGGACG GGAGAAGTGT ACATAGTAAT       2700
Leu Leu
270

TAGTATATAA TCAGAGCAAC CCAGTGGTGG TGATGGTGGT GAAAGAAGAA ACACAGTGAG    2760

ATCCCATTAC GTAGCAGATA AAGCACGTGT GGAGGCGCTG TTCCTCCACT TGCAGTTGCG    2820

GCCATCAATC ATCTTTCCTC TCCTTACTTT CGTCCACCAC AACTCCCATC CTGCCAGCTG    2880

TCGCATCCCC GGGTTGCAAC AACTATCGCC TCCGGGCCT CCGTGGTTCT CCTATATTAT     2940

TCCATCCGAC GGCCGACGTT TCACCCTCAT CCTGCGCCGC CGCAAAATCT CCCCGAGTCG    3000

GTCAACTCCC TCGAACCGCC GCCCGCATCA ACCTCACCGA CCCCCGACCG TCTGCGATCG    3060

TCCAACCGTG CAGCCATGTT CCCTGCCCCG TCACGCTGAT TTGACGCTCA ATTGACTTCC    3120

GTGACATACA TACATACATC CAGCAGCTTA TGATCACAGT TTCCCCGCCT CGTGCCAGTC    3180

CCGCCGCCGC CATTGCCAGC CATGCTATTC TTCCGCGGCG GAGTTAACAG TCCGCGCCGG    3240

CGCAACCAAG AAAAAGCAAT CTTCTGCACC ATTCTCATCA TCTACGCTCT ATACTTCCTC    3300

TTCTTCGCTG GGAGCTCCGA TCCCAAACGG TCAGAGACGT CTGCTGAGGA TGCGGTGAAG    3360

GGAGGCCCGC ATCGGGACTC GCGGTCGGGG AAGGCTTCCC CGTCCGCCTC GGCTTCGCGA    3420

CAGCCCCAGG CCTTGGACAA GGACATGGTG GTGGCTAGTA TGAAGGGAGA CGATGTCTCA    3480

TGGCTGTACA CATACTTTCC TGAGTGGCAC AAAAGCATCT ACGTGGCGGA CGACAAGAAA    3540

GCGCCGTTAA CGGTGGCCTT GAATAAGGGG AGGGAATCGA TGGTGTATCT GACGTGAGTA    3600

GTCTCCTCCG TGTCTTGGCC GGTTCTGGGC GCACCAACTC ACTGCTGCAG               3650

(2) INFORMATION FOR SEQ ID NO:2:

(i) SEQUENCE CHARACTERISTICS:
        (A) LENGTH: 297 amino acids
        (B) TYPE: amino acid
        (D) TOPOLOGY: linear (ii) MOLECULE TYPE: protein (xi) SEQUENCE DESCRIPTION: SEQ ID NO:2:

Met Phe Ser Gly Arg Phe Gly Val Leu Leu Thr Ala Leu Ala Ala Leu
-27         -25                 -20                 -15

Gly Ala Ala Pro Ala Pro Leu Ala Val Arg Ser Val Ser Thr Ser
    -10                  -5                   1               5

Thr Leu Asp Glu Leu Gln Leu Phe Ala Gln Trp Ser Ala Ala Tyr
                10                  15                  20

Cys Ser Asn Asn Ile Asp Ser Lys Asp Ser Asn Leu Thr Cys Thr Ala
```

```
                25                  30                  35

Asn Ala Cys Pro Ser Val Glu Glu Ala Ser Thr Thr Met Leu Leu Glu
            40                  45                  50

Phe Asp Leu Thr Asn Asp Phe Gly Gly Thr Ala Gly Phe Leu Ala Ala
 55                  60                  65

Asp Asn Thr Asn Lys Arg Leu Val Val Ala Phe Arg Gly Ser Ser Thr
 70                  75                  80                  85

Ile Glu Asn Trp Ile Ala Asn Leu Asp Phe Ile Leu Glu Asp Asn Asp
                90                  95                 100

Asp Leu Cys Thr Gly Cys Lys Val His Thr Gly Phe Trp Lys Ala Trp
               105                 110                 115

Glu Ser Ala Ala Asp Glu Leu Thr Ser Lys Ile Lys Ser Ala Met Ser
           120                 125                 130

Thr Tyr Ser Gly Tyr Thr Leu Tyr Phe Thr Gly His Ser Leu Gly Gly
135                 140                 145

Ala Leu Ala Thr Leu Gly Ala Thr Val Leu Arg Asn Asp Gly Tyr Ser
150                 155                 160                 165

Val Glu Leu Tyr Thr Tyr Gly Cys Pro Arg Ile Gly Asn Tyr Ala Leu
                170                 175                 180

Ala Glu His Ile Thr Ser Gln Gly Ser Gly Ala Asn Phe Arg Val Thr
            185                 190                 195

His Leu Asn Asp Ile Val Pro Arg Val Pro Pro Met Asp Phe Gly Phe
            200                 205                 210

Ser Gln Pro Ser Pro Glu Tyr Trp Ile Thr Ser Gly Asn Gly Ala Ser
        215                 220                 225

Val Thr Ala Ser Asp Ile Glu Val Ile Glu Gly Ile Asn Ser Thr Ala
230                 235                 240                 245

Gly Asn Ala Gly Glu Ala Thr Val Ser Val Leu Ala His Leu Trp Tyr
                250                 255                 260

Phe Phe Ala Ile Ser Glu Cys Leu Leu
                265                 270

(2) INFORMATION FOR SEQ ID NO:3:

(i) SEQUENCE CHARACTERISTICS:
        (A) LENGTH: 32 base pairs
        (B) TYPE: nucleotide
        (C) STRANDEDNESS: single-stranded
        (D) TOPOLOGY: linear (ii) MOLECULE TYPE: genomic DNA (iii) HYPOTHETICAL: No (iv) ANTI-SENSE: No (ix) FEATURE:
        (A) NAME/KEY: misc_feature
        (B) LOCATION: 18
        (D) OTHER INFORMATION: /product= "N is inosine"

(ix) FEATURE:
        (A) NAME/KEY: misc_feature
        (B) LOCATION: 24
        (D) OTHER INFORMATION: /product= "N is inosine"

(ix) FEATURE:
        (A) NAME/KEY: misc_feature
        (B) LOCATION: 30
        (D) OTHER INFORMATION: /product= "N is inosine"

(xi) SEQUENCE DESCRIPTION: SEQ ID NO:3:

TCCAAGCTTG ACGAACTNCA ACTNTTCGCN CA                                      32
```

(2) INFORMATION FOR SEQ ID NO:4:

(i) SEQUENCE CHARACTERISTICS:
        (A) LENGTH: 40 base pairs
        (B) TYPE: nucleotide
        (C) STRANDEDNESS: single-stranded
        (D) TOPOLOGY: linear     (ii) MOLECULE TYPE: genomic DNA     (iii) HYPOTHETICAL: No     (iv) ANTI-SENSE: No     (ix) FEATURE:
        (A) NAME/KEY: misc_feature
        (B) LOCATION: 40
        (D) OTHER INFORMATION: /product= "N is A, C or G"

(xi) SEQUENCE DESCRIPTION: SEQ ID NO:4:

GACTCGAGTC GACATCGATT TTTTTTTTTT TTTTTTTTTN     40

(2) INFORMATION FOR SEQ ID NO:5:

(i) SEQUENCE CHARACTERISTICS:
        (A) LENGTH: 20 base pairs
        (B) TYPE: nucleotide
        (C) STRANDEDNESS: single-stranded
        (D) TOPOLOGY: linear     (ii) MOLECULE TYPE: genomic DNA     (iii) HYPOTHETICAL: No     (iv) ANTI-SENSE: No     (xi) SEQUENCE DESCRIPTION: SEQ ID NO:5:

GACTCGAGTC GACATCGATT     20

(2) INFORMATION FOR SEQ ID NO:6:

(i) SEQUENCE CHARACTERISTICS:
        (A) LENGTH: 42 base pairs
        (B) TYPE: nucleotide
        (C) STRANDEDNESS: single-stranded
        (D) TOPOLOGY: linear     (ii) MOLECULE TYPE: genomic DNA     (iii) HYPOTHETICAL: No     (iv) ANTI-SENSE: No     (xi) SEQUENCE DESCRIPTION: SEQ ID NO:6:

GGAATTCACC TGCTAACCAT GTTCTCTGGA CGGTTTGGAG TG     42

(2) INFORMATION FOR SEQ ID NO:7:

(i) SEQUENCE CHARACTERISTICS:
        (A) LENGTH: 24 base pairs
        (B) TYPE: nucleotide
        (C) STRANDEDNESS: single-stranded
        (D) TOPOLOGY: linear     (ii) MOLECULE TYPE: genomic DNA     (iii) HYPOTHETICAL: No     (iv) ANTI-SENSE: No     (xi) SEQUENCE DESCRIPTION: SEQ ID NO:7:

```
CGCCAGGGTT TTCCCAGTCA CGAC                                                24
```

(2) INFORMATION FOR SEQ ID NO:8:

(i) SEQUENCE CHARACTERISTICS:
        (A) LENGTH: 28 amino acids
        (B) TYPE: amino acid
        (C) STRANDEDNESS: single
        (D) TOPOLOGY: linear     (ii) MOLECULE TYPE: protein     (xi) SEQUENCE DESCRIPTION: SEQ ID NO:8:

```
Ser Val Ser Thr Ser Thr Leu Asp Glu Leu Gln Leu Phe Ala Gln Trp
1               5                   10                  15

Ser Ala Ala Ala Tyr Cys Ser Asn Asn Ile Asp Ser
            20                  25
```

(2) INFORMATION FOR SEQ ID NO:9:

(i) SEQUENCE CHARACTERISTICS:
        (A) LENGTH: 13 amino acids
        (B) TYPE: amino acid
        (C) STRANDEDNESS: single
        (D) TOPOLOGY: linear     (ii) MOLECULE TYPE: protein     (xi) SEQUENCE DESCRIPTION: SEQ ID NO:9:

```
Glu His Ile Thr Ser Gln Gly Ser Gly Ala Asn Phe Arg
1               5                   10
```

(2) INFORMATION FOR SEQ ID NO:10:

(i) SEQUENCE CHARACTERISTICS:
        (A) LENGTH: 27 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:10:

```
CTCGTGTAGT GGAGGGTCCC GAGGCGG                                             27
```